(12) United States Patent
Dasi et al.

(10) Patent No.: US 11,224,509 B2
(45) Date of Patent: Jan. 18, 2022

(54) PROSTHETIC HEART VALVE WITH TRI-LEAFLET DESIGN FOR USE IN PERCUTANEOUS VALVE REPLACEMENT PROCEDURES

(71) Applicants: Ohio State Innovation Foundation, Columbus, OH (US); Lakshmi Prasad Dasi, Dublin, OH (US); Atieh Yousefi Koupaei, Columbus, OH (US); Megan Kristine Heitkemper, Columbus, OH (US)

(72) Inventors: Lakshmi Prasad Dasi, Dublin, OH (US); Atieh Yousefi Koupaei, Columbus, OH (US); Megan Kristine Heitkemper, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 93 days.

(21) Appl. No.: 16/625,456

(22) PCT Filed: Jun. 29, 2018

(86) PCT No.: PCT/US2018/040421
§ 371 (c)(1),
(2) Date: Dec. 20, 2019

(87) PCT Pub. No.: WO2019/006383
PCT Pub. Date: Jan. 3, 2019

(65) Prior Publication Data
US 2021/0145573 A1 May 20, 2021

Related U.S. Application Data

(60) Provisional application No. 62/565,709, filed on Sep. 29, 2017, provisional application No. 62/527,640, filed on Jun. 30, 2017.

(51) Int. Cl.
*A61F 2/24* (2006.01)

(52) U.S. Cl.
CPC .......... *A61F 2/2418* (2013.01); *A61F 2/2415* (2013.01); *A61F 2/2433* (2013.01); *A61F 2210/0004* (2013.01); *A61F 2240/001* (2013.01)

(58) Field of Classification Search
CPC ................................ A61F 2/24; A61F 2/2418
(Continued)

(56) References Cited

U.S. PATENT DOCUMENTS

| 10,966,826 B2 * | 4/2021 | Hofferberth .......... A61F 2/2418 |
| 2006/0020327 A1 * | 1/2006 | Lashinski .......... A61B 17/0644 623/1.25 |

(Continued)

FOREIGN PATENT DOCUMENTS

| JP | 2008-539985 A | 11/2008 |
| JP | 2013-163037 A | 8/2013 |

OTHER PUBLICATIONS

International Search Report and Written Opinion issued in PCT application No. PCT/US2018/040421, dated Jan. 16, 2019.
(Continued)

*Primary Examiner* — Suzette J Gherbi
(74) *Attorney, Agent, or Firm* — Benesch, Friedlander, Coplan & Aronoff LLP

(57) ABSTRACT

A transcatheter prosthetic heart valve includes a stent frame and at least one sheet of leaflet material formed in to a tube, which includes a lower portion disposed on an exterior of the stent frame and an upper edge portion disposed within the stent frame. The upper edge portion includes at least a portion configured to wrap around a first portion of the top edge of the stent frame and fold towards an exterior of the stent frame. The upper edge portion also includes at least
(Continued)

another portion configured to weave through the stent frame and fold towards the interior of the stent frame.

16 Claims, 12 Drawing Sheets

(58) Field of Classification Search
USPC .............................................. 623/2.18–2.19
See application file for complete search history.

(56) References Cited

U.S. PATENT DOCUMENTS

| | | | |
|---|---|---|---|
| 2006/0047338 A1 | 3/2006 | Jensen et al. | |
| 2012/0059454 A1* | 3/2012 | Millwee | A61F 2/2418 623/1.24 |
| 2012/0271398 A1* | 10/2012 | Essinger | A61F 2/2418 623/1.11 |
| 2013/0131793 A1 | 5/2013 | Quadri et al. | |
| 2013/0144382 A1 | 6/2013 | DeStefano | |
| 2013/0325117 A1 | 12/2013 | Bruchman et al. | |
| 2014/0172086 A1* | 6/2014 | Quadri | A61F 2/2418 623/2.38 |
| 2014/0277427 A1* | 9/2014 | Ratz | A61F 2/2418 623/2.38 |
| 2015/0196688 A1* | 7/2015 | James | A61L 17/10 623/2.12 |
| 2017/0049566 A1 | 2/2017 | Zeng et al. | |
| 2020/0360135 A1* | 11/2020 | Hofferberth | A61F 2/2412 |
| 2020/0368017 A1* | 11/2020 | Hofferberth | A61F 2/2418 |
| 2020/0368018 A1* | 11/2020 | Benichou | A61F 2/2412 |

OTHER PUBLICATIONS

International Preliminary Report on Patentability issued in PCT application No. PCT/US2018/040421, dated Dec. 31, 2019.
Extended European Search Report issued in EP Application No. 18824870.2, dated Feb. 11, 2021.

* cited by examiner

PROSTHETIC HEART VALVE WITH TRI-LEAFLET DESIGN FOR USE IN PERCUTANEOUS VALVE REPLACEMENT PROCEDURES

CROSS REFERENCE OF RELATED APPLICATION

This application claims the benefit of U.S. Provisional Patent Application No. 62/527,640, filed Jun. 30, 2017, and U.S. Provisional Patent Application No. 62/565,709, filed Sep. 29, 2017, which are incorporated herein by reference in entirety.

GOVERNMENT SPONSORSHIP

The invention was made with government support under grant number HL119810 awarded by the National Institutes of Health. The government has certain rights in the invention.

FIELD OF THE INVENTION

The present invention relates to the manufacture and use of a prosthetic valve for use in the human heart. More specifically, the invention relates to the manufacture and use of a tri-leaflet prosthetic heart valve that may be used in percutaneous valve replacement procedures.

BACKGROUND

Heart valve replacement is the second most common cardiac operation performed in the United States. Currently, over four million people are diagnosed with heart valve disorder across the world, each year. Moreover, heart disease is prevalent in about 2.5% of the overall United States population, and 10.4% of its elderly population.

Typically, prosthetic heart valves used in aortic heart valve replacement procedures are either mechanical or bioprosthetic. However, these valves introduce significant risk of thromboembolism, requiring the patient to undergo lifelong anticoagulation therapy, or the patient become more prone to valve degeneration and tissue failure, requiring reoperation. It would be useful to produce a prosthetic heart valve that would be durable, while not necessitating anticoagulation therapy.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

A transcatheter prosthetic heart valve including a stent frame having a top portion and a bottom portion; and a tube of leaflet material configured to encircle the stent frame is provided. The tube of leaflet material includes a lower portion disposed about an exterior surface of the stent frame; and an upper portion that is at least partially disposed within an interior surface of the stent frame; and wherein the upper portion disposed within the stent frame forms at least one leaflet capable of moving from a first position to a second position within the stent frame.

Moreover, at least a portion of the upper portion of the leaflet material is configured to wrap around a connection point of the top portion and to fold towards the interior surface of the stent frame. And, at least a second portion of the tube of leaflet material is configured to weave under an upper edge of the top portion of the stent frame, folding towards the interior surface of the stent frame.

In another embodiment, the tube of leaflet material is formed from a continuous sheet of leaflet material, and an upper edge of the continuous sheet of leaflet material comprises at least three arches extending upwardly therefrom. Alternatively, the tube of leaftlet material may be formed from two or more pieces of leaflet material.

In another embodiment, the upper edge of the continuous sheet of leaflet material comprises a space between every two directly adjacent arches of the at least three arches.

In another embodiment, the tube of leaflet material is extruded so that the tube does not have a side seam. The material may be made of a polymer material. That polymer material may be linear low density polyethylene, polytetrafluoroethylene, low-density polyethylene, polyethylene terephthalate, polypropylene, polyurethane, polycaprolactone, polydimethylsiloxane, polymethylmethacrylate, polyoxymethylene, thermoplastic polyurethane, and combinations thereof. The leaflet material may further include a polymer material and hyaluronic acid. It may also include a bioprosthetic material.

In another embodiment the leaflets may have a three dimensional curvature or a two dimensional curvature.

The stent frame may be self-expandable or may be expanded manually using a balloon. The stent frame may have a height and an inner diameter, wherein a ratio of the height to the inner diameter is in a range between about 0.5 and about 0.9. However, it should be appreciated that the stent may be made to conform to the natural geometry of the patient's body.

DETAILED DESCRIPTION

The disclosed embodiments are directed to a prosthetic heart valve. In particular, a prosthetic heart valve having a tri-leaflet design for use in a percutaneous (or transcatheter) valve replacement procedure (hereinafter "TPHV") in order to replace either a failing or damaged native aortic or mitral heart valve in a patient is provided. Although a TPHV with a tri-leaflet design will be described herein, it should be apparent to one of skill in the art that any number of leaflets may be made using the TPHV. The TPHV disclosed herein may generally include one or more leaflets disposed on a stent frame, as shown in FIGS. 1-4. The leaflets are configured simulate a patient's native leaflets and to open and close in response to the pumping of the heart. When leaflets are closed, as shown in FIG. 4, the commissures meet to ensure minimal reverse flow of the blood.

In certain embodiments, the TPHV will provide a prosthetic valve with a higher effective orifice compared to other prosthetic valves that are commercially available. In certain embodiments, the TPHV will provide improved flow characteristics through the geometric design of both the stent frame and the leaflet. The designs of the stent frame in combination with the designs of the leaflet(s) enable improved performance over other commercially available prosthetic valves. For example, the designs of the leaflet(s) and/or the manners in which the leaflet(s) is disposed on the stent frame may improve durability of the TPHV, reduce the number of sutures required to assemble the leaflet(s), and/or improve leaflet coaptation.

Figure 1:
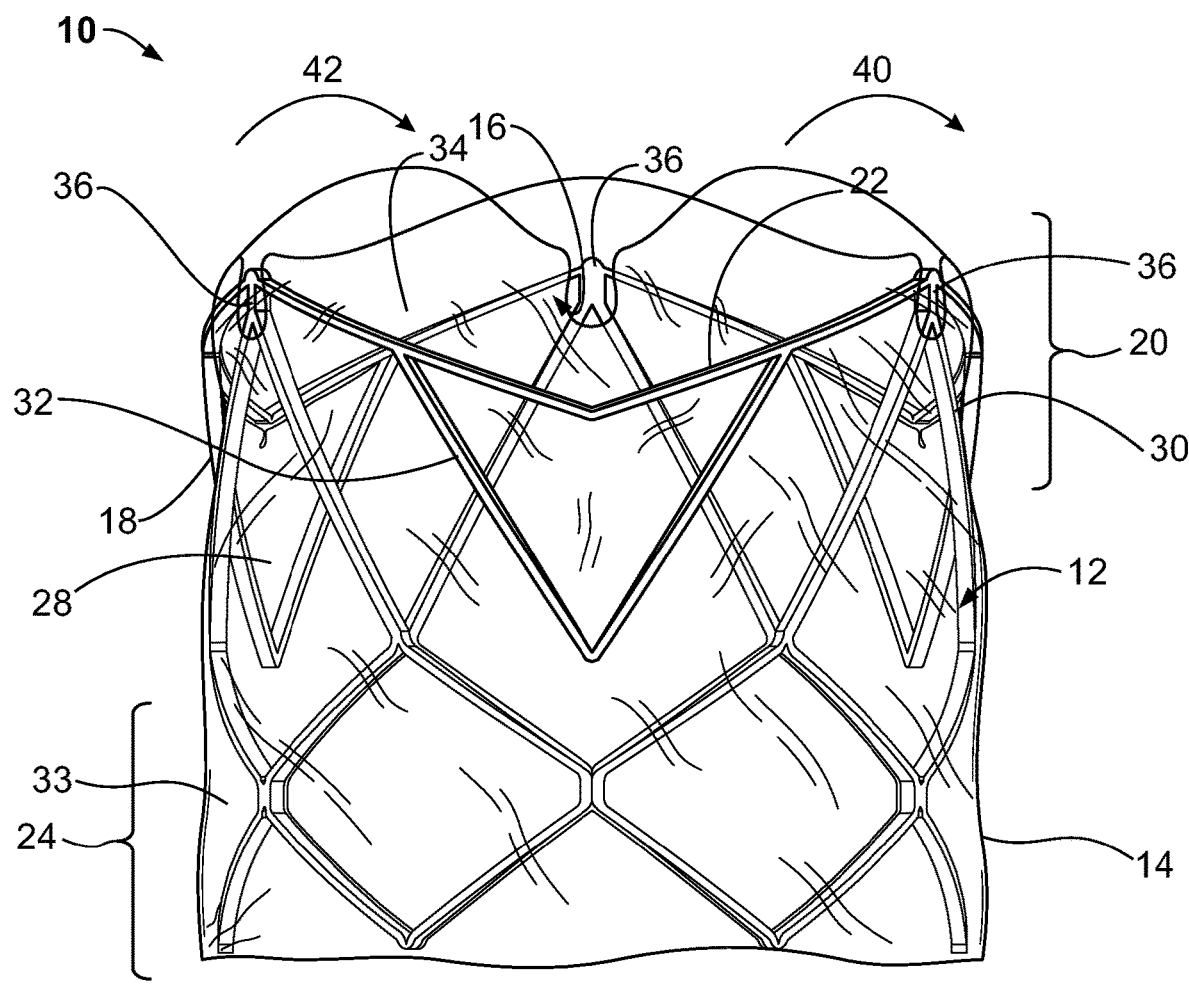
FIG. 1 is a front view of the transcatheter prosthetic heart valve of one embodiment of the present disclosure with the leaflets in an open position.
Figure 2:
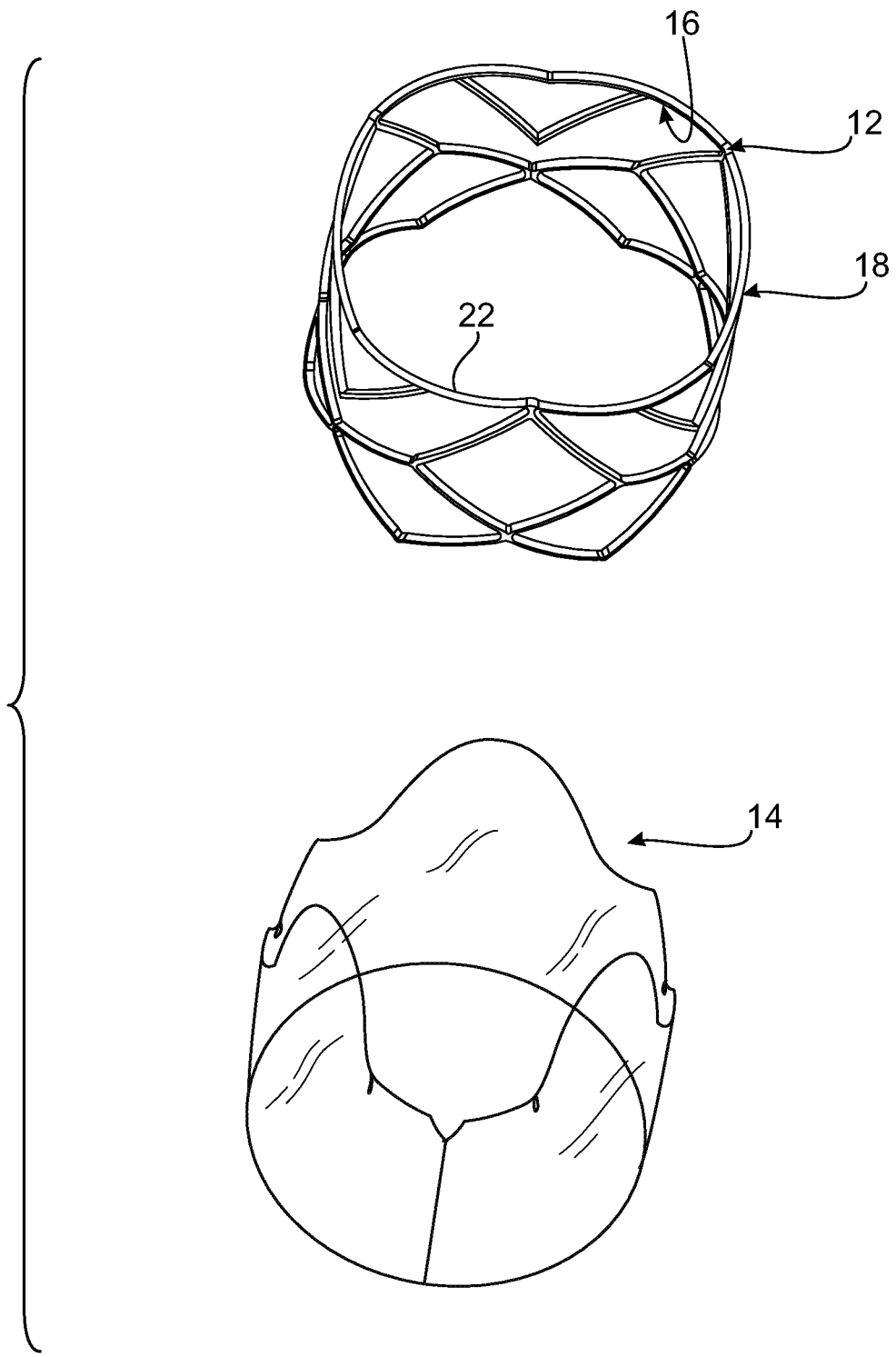
FIG. 2 is an exploded view of the transcatheter prosthetic heart valve of FIG. 1, including a stent frame and a sheet of leaflet material.
Figure 3:
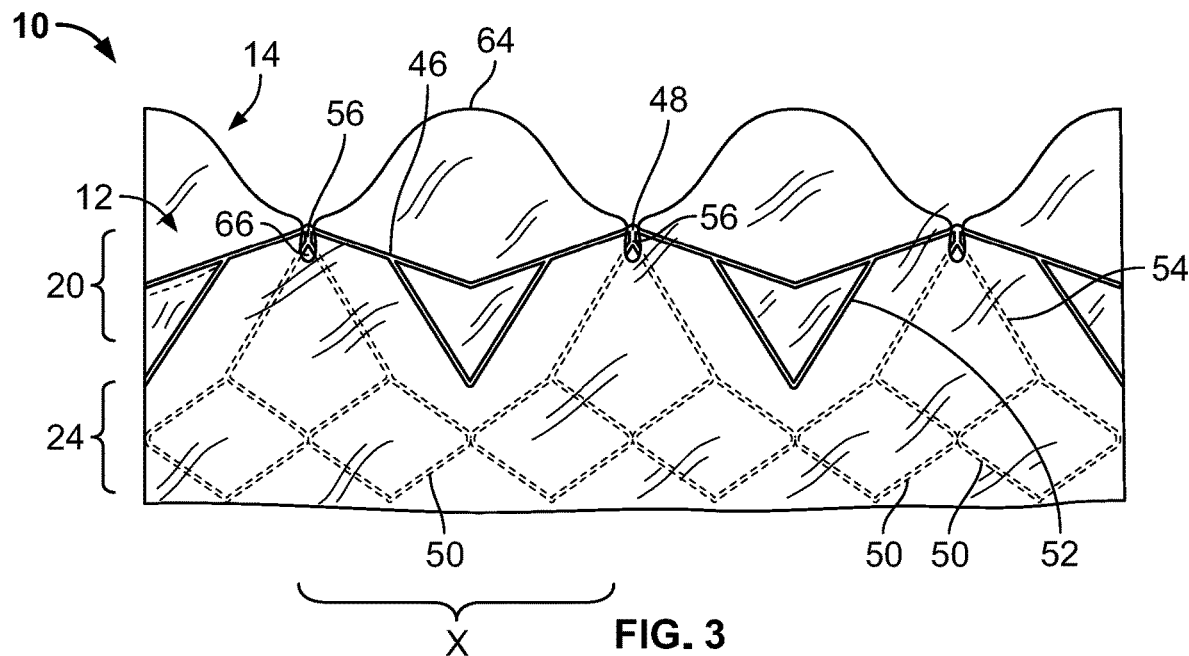
FIG. 3 is a plan view of the stent frame of FIG. 1, in accordance with an embodiment of the present disclosure.
Figure 4:
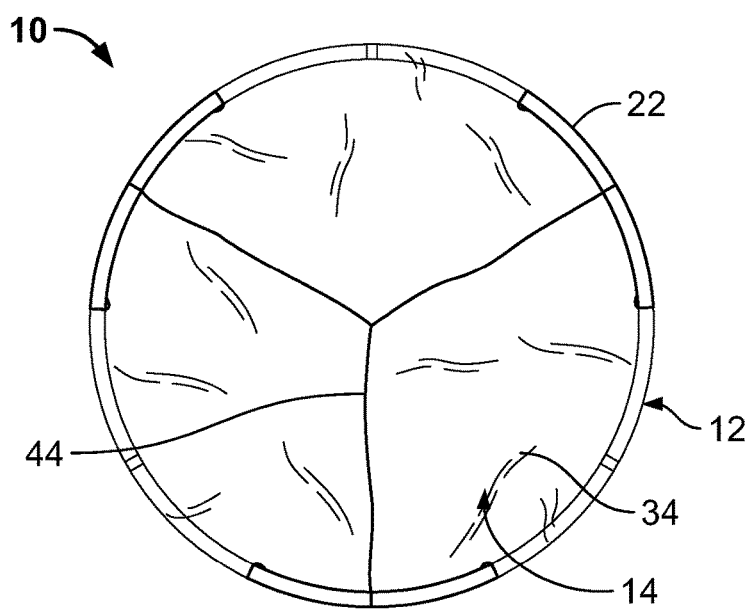
FIG. 4 is a top view of the transcatheter prosthetic heart valve of FIG. 1 with the leaflets in a closed position.
Figure 5:
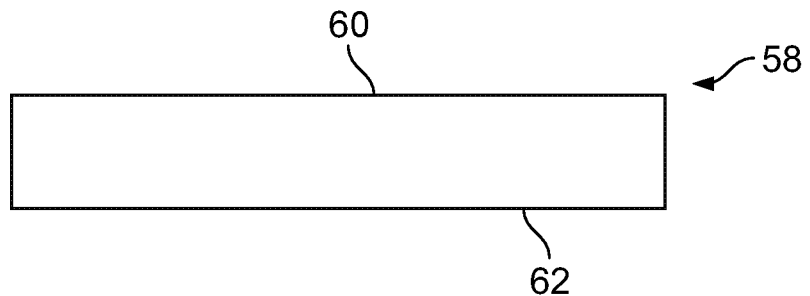
FIG. 5 is a plan view of an embodiment of the sheet of leaflet material, in accordance with an embodiment of the present disclosure.
Figure 6:
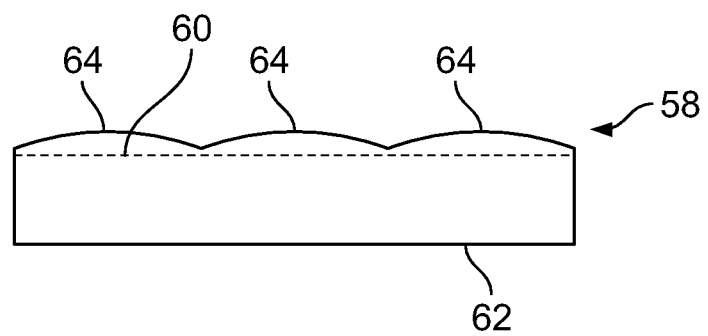
FIG. 6 is a plan view of another embodiment of the sheet of leaflet material, in accordance with an embodiment of the present disclosure.
Figure 7:
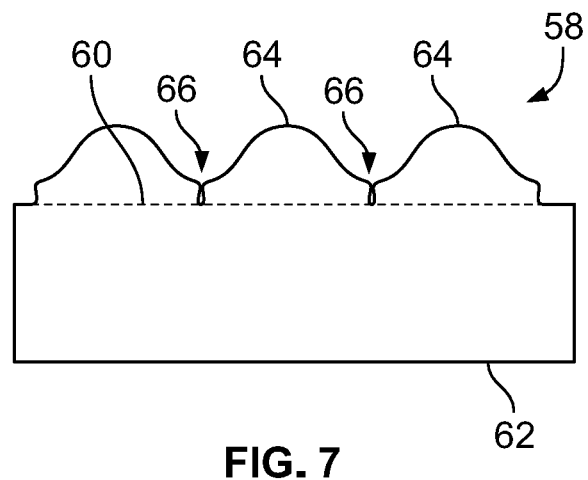
FIG. 7 is a plan view of an embodiment of the sheet of leaflet material, in accordance with an embodiment of the present disclosure.

Referring now to FIGS. 1-4, FIG. 1 illustrates a perspective view of on embodiment of the TPHV 10 including a stent frame 12 and a sheet of leaflet material 14 (as shown in FIG. 5, 6, or 7) formed in to a tube of leaflet material. FIG. 2 is an exploded view of the TPHV 10 of FIG. 1, showing the stent frame or frame 12 and the sheet of leaflet material 14.

As illustrated in FIGS. 1 and 2, the stent frame 12 includes an interior or an inner surface 16, an exterior or outer surface 18, a top portion 20 having a top edge 22, and a bottom portion 24. The tube of leaflet material 14 may be disposed on the exterior 18 of the stent frame 12. However, as the tube of leaflet material 14 is placed on to the stent frame 12 by sliding the tube onto the stent frame 12 from the bottom portion 24 of the frame to the top portion 20, in proximity to the top edge 22 of the top portion 20, the tube of leaflet material 14 is configured to bend or fold towards the interior 16 of the stent frame 12. In the illustrated embodiment, an upper portion 28 of the tube of leaflet material 14 bends or folds around a first portion 30 of the top portion 20 of the stent frame 12 and tucks or is woven under a second portion 32 of the top portion 20 of the stent frame 12 at its top edge 22 (e.g., at least a portion of the sheet of the leaflet material 14 weaves through the stent frame 12) to form leaflets 34, while a lower portion 33 of the tube of leaflet material 14 is disposed on the exterior 18 of the stent frame 12. In the illustrated embodiment, the second portion 32 of the top portion 20 of the stent frame 12 is disposed between upper connection points 36 of the stent frame 12, which connect the top portion 20 of the stent frame to a middle (not shown) or bottom portion 24 of the stent frame 12.

Herein, the part of the leaflet material 14 that wraps under the top edge 22 of the stent frame 12 and folds towards the interior 16 of the stent frame 12 is referred to as a leaflet 34. As set forth above, the TPHV may have a tri-leaflet design or other designs with any suitable number of leaflets. The leaflets 34 may flex generally in a first direction 40 and open to a first position to allow forward flow of blood and may flex generally in a second direction 42 to close to a second position and block reverse flow of the blood. When the leaflets 34 are closed, commissures 44 (as shown in FIG. 4) meet to ensure minimal reverse flow of the blood.

The tube of material 14 woven through the stent frame 12, and thus forming leaflets 34, is to a degree constrained by the top edge 22 of the stent frame 12. In addition, the geometry and/or design of the top edge 22 may contribute to shaping the leaflet material 14 into desired shapes of the leaflets 34 for better coaptation. As a result, the number of sutures required to assemble the TPHV 10 may be significantly reduced.

Furthermore, as the sheet of leaflet material 14 is woven through the stent frame 12, at least a portion (e.g., the second portion 32) of the top edge 22 may provide mechanical support and/or reinforcement as the leaflets 34 go through cycles of opening and closing, which may result in improved durability of the TPHV 10.

With the foregoing in mind, the stent frame 12 may be formed of a single piece of material or it may be formed of multiple wires which are welded, or otherwise suitably connected, to form a single stent frame 12.

The stent frame 12 may have various geometric designs. With regard to the stent frame shown in FIGS. 1-4, and with specific reference to FIG. 3, the stent frame may include a top portion 20 comprised of undulating plurality of similarly sized wires or struts 46, connected at the respective apexes 48. The stent frame 12 may further include a bottom portion 24 including a plurality of wires or struts formed in to a repeating diamond 50 pattern. Between the top portion 20 and the bottom portion 24, the stent frame 12 may further include a set of struts formed in to V-shaped struts 52 extending downwardly from the top portion 20 and disposed between the apexes 48 of the top portion 20. And finally, the stent frame 12 may include a set of struts formed in to inverted V-shaped struts 54 disposed between two of the diamonds 50 formed in to the bottom portion 24 and connected to the top portion 20 of the stent frame 12 at connection points 56. Each of the connection points 56 may be located at each of the apexes 48 of the top portion 20.

The top portion 20, bottom portion 24, and middle V-shaped struts 52, 54 together form three primary units X of the stent frame 12; however, in certain embodiments, the stent frame 12 may include less than or more than three units X as appropriate.

As shown in FIGS. 1, 2, 3 and 4, the ends of the flat stent frame are connected to form a tubular stent frame 12 that can be inserted into the body of a patient. The stent frame 12 may be made of stainless steel, nitinol, cobalt chromium, or other suitable material. It should be understood that the shape of the frame 12 may be generally circular in nature or it may be elliptical, oval, or other shape suitable to the curvature of the patient's valve annulus.

Referring now to FIGS. 5, 6, and 7, the tube of leaflet material 14 of the TPHV 10 may be created using a single piece of polymeric or bioprosthetic (such as porcine or bovine pericardium) material. It will also be understood that the tube of leaflet material 14 may also be created using separate pieces of leaflet material affixed between each unit X of the stent frame 12.

As shown in FIG. 5, in one embodiment, a continuous sheet of leaflet material 58 may include an upper edge portion 60 and a lower edge portion 62. The lower edge portion 62 may be generally rectangular in shape. The upper edge portion 60 may be generally rectangular in shape, or as will be discussed below and shown in FIGS. 6 and 7, the upper edge portion may include at least one arch 64 extending upwardly therefrom.

The leaflet material 58 may be made of a polymeric material, such as linear low density polyethylene (LLDPE), polytetrafluoroethylene (PTFE), low-density polyethylene (LDPE), polyethylene terephthalate (PET), polypropylene (PP), polyurethane, polycaprolactone (PCL), polydimethylsiloxane (PDMS), polymethylmethacrylate (PMMA), polyoxymethylene (POM), thermoplastic polyurethane, and combinations thereof. In one embodiment, the leaflet material 58 may be made of a polymeric material, such as LLDPE, that includes hyaluronic acid to prevent blood clot and thrombosis formation. An example of this material is disclosed in U.S. application Ser. No. 14/381,332, entitled Glycosaminoglycan and Synthetic Polymer Material for Blood-Contacting Applications, which is incorporated herein by reference in its entirety.

As set forth above, the leaflet material 58 may be woven through each unit X of the frame 12. Specifically, the leaflet material 58 may be woven through the frame 12 so that a majority of the material 58 is disposed on the outer surface 18 of the frame 12 and a portion of the material 58 is tucked inside the frame 12 between the upper connection points 36, as shown in FIG. 1. In doing so, the leaflets 34 are formed and disposed with their outer surface against the inner surface 16 of the frame 12.

In one embodiment, the leaflet material 58 is secured to the frame 12 by suturing the material 58 to the frame 12 at the connection points 56 between the top portion 20 and the inverted V-shaped struts 54 and between every other diamond 50 of the bottom portion 24. By using a single continuous piece of leaflet material 58 mounted around the stent frame 12, the number of sutures required to assemble the leaflets 34 is reduced. However, it should be appreciated that more sutures may be used at any point on the stent frame or that multiple pieces of leaflet material may be mounted about the circumference of the stent frame 12.

As shown in FIGS. 6 and 7, the leaflet material 58 may include the upper edge portion 60 with a plurality of arches 64 (e.g., at least two arches 64, at least three arches 64). It should be understood that the arches 64 may be formed integrally with the single sheet of leaflet material 58 or may be attached to the upper edge portion 60 after the material is formed. The arches 64 on the upper edge portion 60 provide arched leaflets 34 when wrapped around the stent frame 12. Through the use of arched leaflets 34, it was discovered that flow reattachment is facilitated and recirculation regions that are directly related to thrombus formation are decreased. In addition, the use of arched leaflets 34 provides an improved leaflet coaptation.

As shown in FIGS. 3 and 7, the leaflet material 58 may include one or more spaces or grooves 66 in the upper edge portion 60, and the spaces or grooves 66 are disposed between each pair of directly adjacent arches 64. The one or more spaces 66 are configured to improve coaptation of the leaflets 34.

For example, the one or more spaces 66 may help to accommodate the opening and closing motions of the leaflets 34, such that the commissures (e.g., the upper edge portion 60) meet with better conformity to achieve better coaptation and ensure minimal reverse flow of the blood when the leaflets 34 are closed, as shown in FIG. 4.

Referring again to FIG. 1, the tube of leaflet material 14 may be woven through the stent frame 12 in a manner that each of the arches 64 is tucked in or folded under the second portion 32 of the top edge 22 while each of the spaces 66 is approximately aligned with the corresponding upper connection point 36. As such, the one or more spaces 66 may provide flexibility and better conformity where the leaflet material 58 (the sheet of leaflet material 14) transitions from portions that are tucked in under (at the second portion 32 of the top edge 22) the stent frame 12 to portions that wrap around (at the first portion 30 of the top edge 22) the stent frame 12.

Once the sheet of leaflet material 58 is installed onto the stent frame 12, the leaflets 34 may be further formed or shaped by applying a combination of heat and pressure to the once planar sheet of leaflet 14. This treatment can be used to further change the shape of the sheet of leaflet 14 into a three dimensional configuration (as is the case for native valve leaflets) (not shown). In one embodiment, vacuum pressure is applied to the formed TPHV 10 on the upstream side of the TPHV 10 to force the sheet of leaflet 14 (the leaflets 34 in particular) to close. Subsequently, heat is applied from the downstream side in order to make the polymer (which is a thermoplastic) relax and stretch under the forces exerted by the vacuum. The resulting shape of the sheet of leaflet 14, and the leaflets 34 in particular, may more closely resemble the patent's native leaflet shape.

As will be appreciated from the description below, the stent frame may have different geometric designs, examples of which are shown in FIGS. 8-21, that allow at least a portion of the leaflet material to be disposed about the exterior of the stent frame, while at least another portion is woven within the stent frame to form leaflets on the interior surface.

Figure 8:
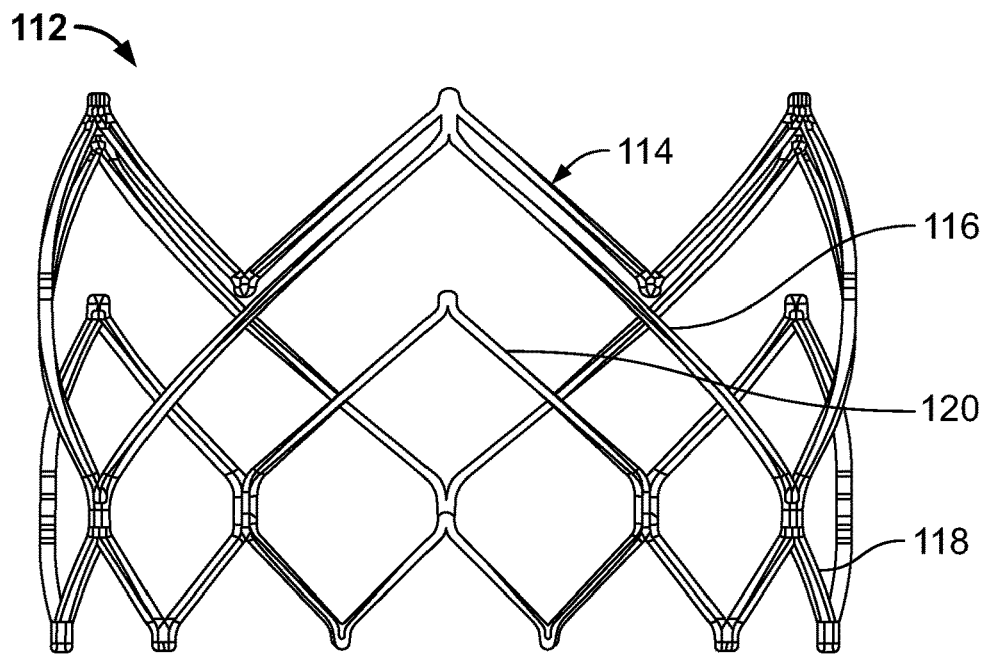
FIGS. 8, 9, and 10 are respectively a front view, a perspective view, and a plan view of another embodiment of the stent frame, in accordance with an embodiment of the present disclosure.
Figure 9:
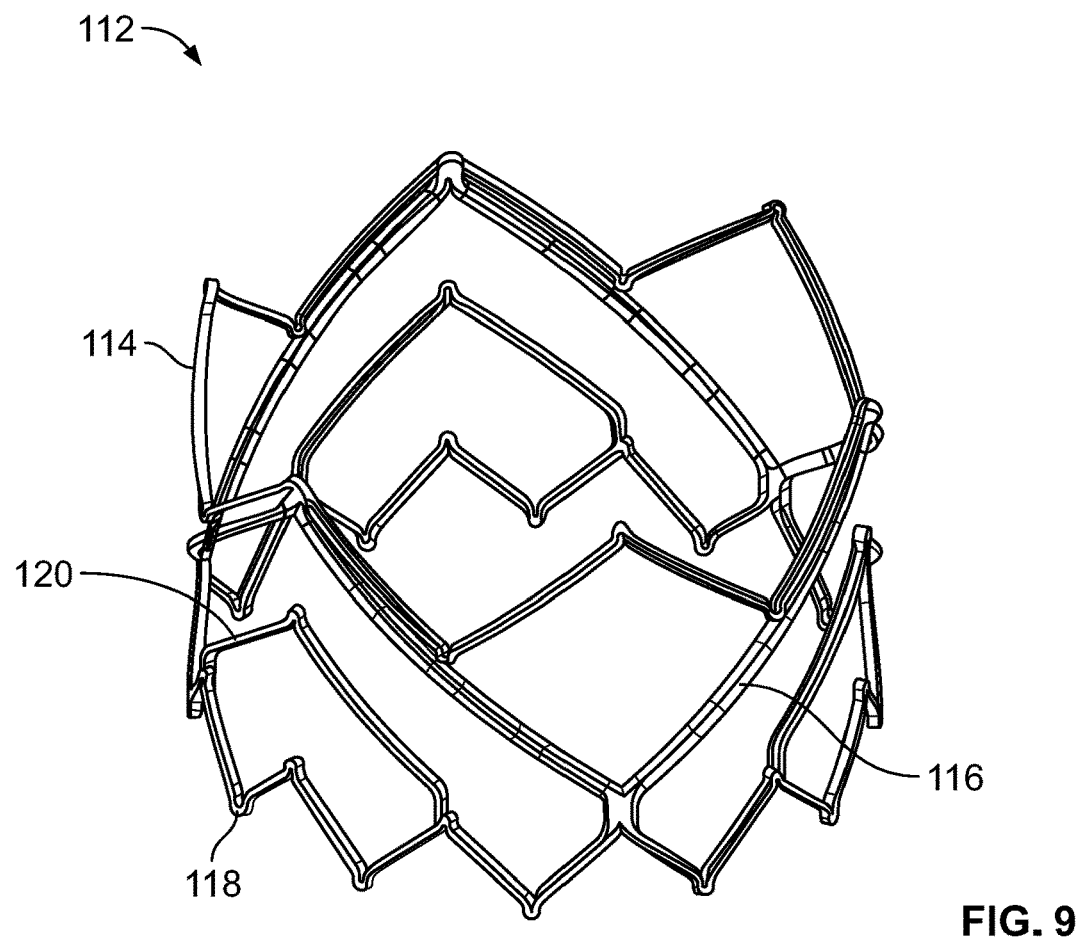
Figure 10:
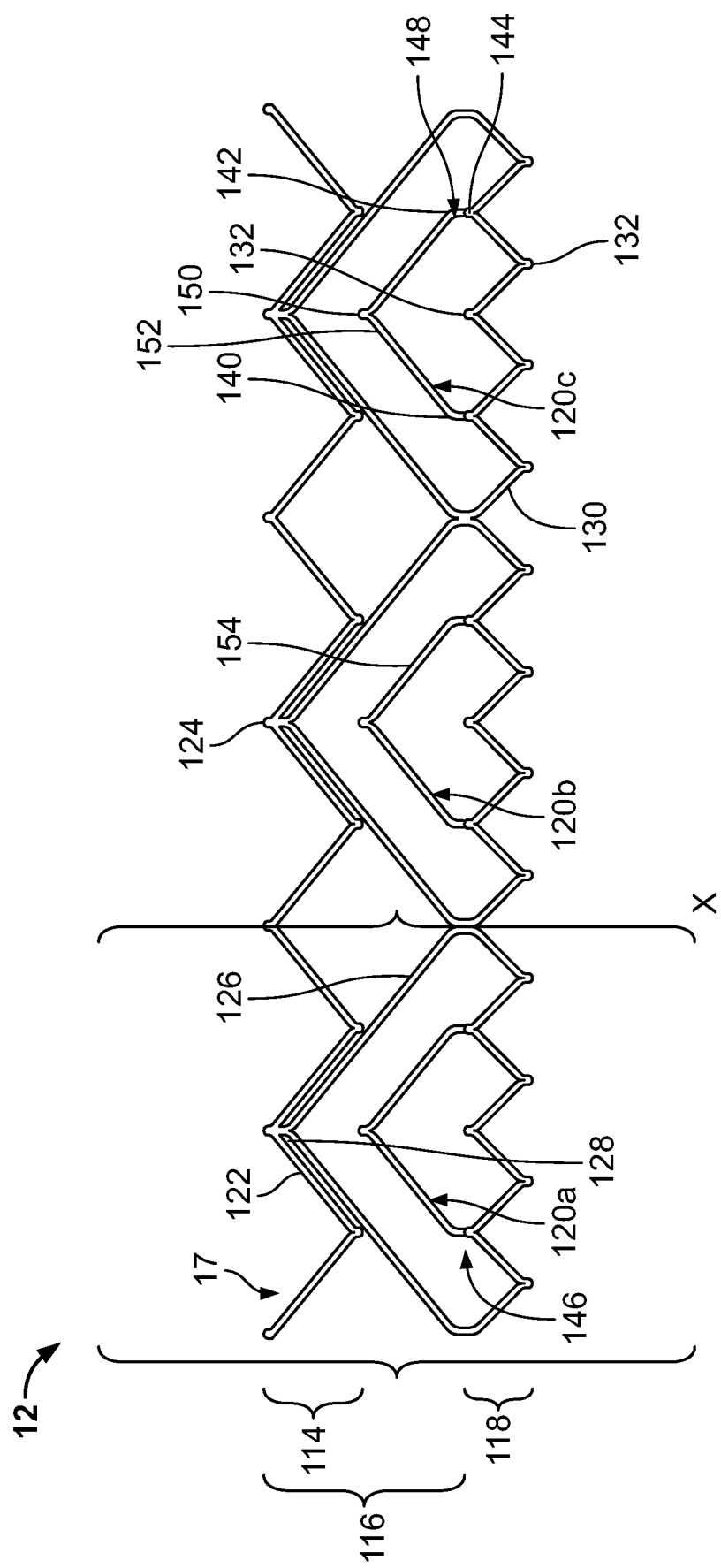

Referring now to FIGS. 8, 9, and 10, and with specific reference to FIG. 10, in another embodiment, a stent frame 112 may include a top, middle, and bottom row of wires (114, 116, 118) and a set of wire connectors (120a, 120b, 120c) that together form the three primary units X of the stent frame 112. The top row 114 of the frame 112 is comprised of an undulating plurality of similarly sized medium-length wires (or struts) 122, connected at the respective apexes 124. The wires (or struts) may be welded together or may be formed of a single piece of laser cut material.

In this embodiment, the top row 114 includes twelve such wires of about 8.14 millimeters (mm) in length—four wires in each unit X of the stent frame. In the illustrated embodiment, the stent frame 112 includes at least three units X; however, in certain embodiments, the stent frame 112 may include less than or more than three units X as appropriate.

The middle row 116 is generally comprised of a plurality of similarly sized extended-length wires 126, connected to one another at the respective apexes 128. In this embodiment, the middle row 116 includes six such wires of about 17.45 mm in length—two wires in each unit X of the stent frame 112.

The bottom row 118 is generally comprised of a plurality of similarly sized short-length wires 130, connected to one another at the respective apexes 132. In this embodiment, the bottom row 118 includes twenty-four such wires of about 3.96 mm in length—eight wires in each unit X of the stent frame 112.

When assembled, the middle row of wires (or struts) 116 is connected to the top row 114 by connecting each upwardly extending apex 128 of the middle row 116 to every other upwardly extending apex 124 of the upper row 114 to form three upper connection points 134—one in each unit X. And, the middle row 116 is connected to the bottom row 118 by connecting each downwardly extending apex of the middle row 116 to every first and fifth upwardly extending apex 132 of the bottom row 118 to form lower connection points 136—two in each unit X.

The stent frame 112 also includes a secondary set of wire connectors (120a, 120b, 120c) that are connected to the bottom row 118. The secondary set of wire connectors 120a, 120b, 120c may have a first terminal end 140 and second terminal end 142 that are connected to every second and fourth upwardly extending apex of the bottom row 118 to form secondary connection points 144—two in each unit X. Generally, the secondary connectors 120a, 120b, 120c are shaped to extend upwardly from each terminal end 140, 142 along first and second struts 146 and 148 and to connect at a pinnacle 150 along a third and fourth strut 152, 154 in a roof-shaped design.

Figure 11:
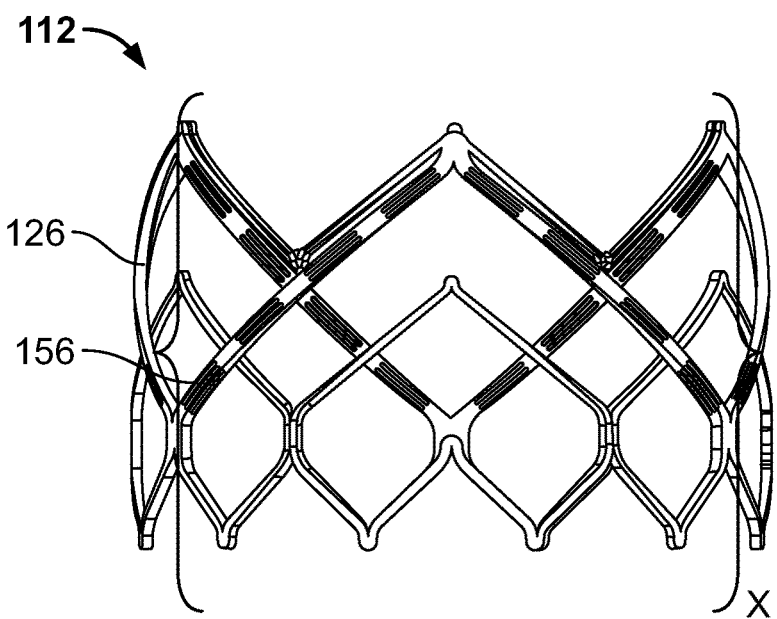
FIGS. 11 and 12 are respectively a front view and a perspective view of another embodiment of the stent frame, in accordance with an embodiment of the present disclosure.
Figure 12:
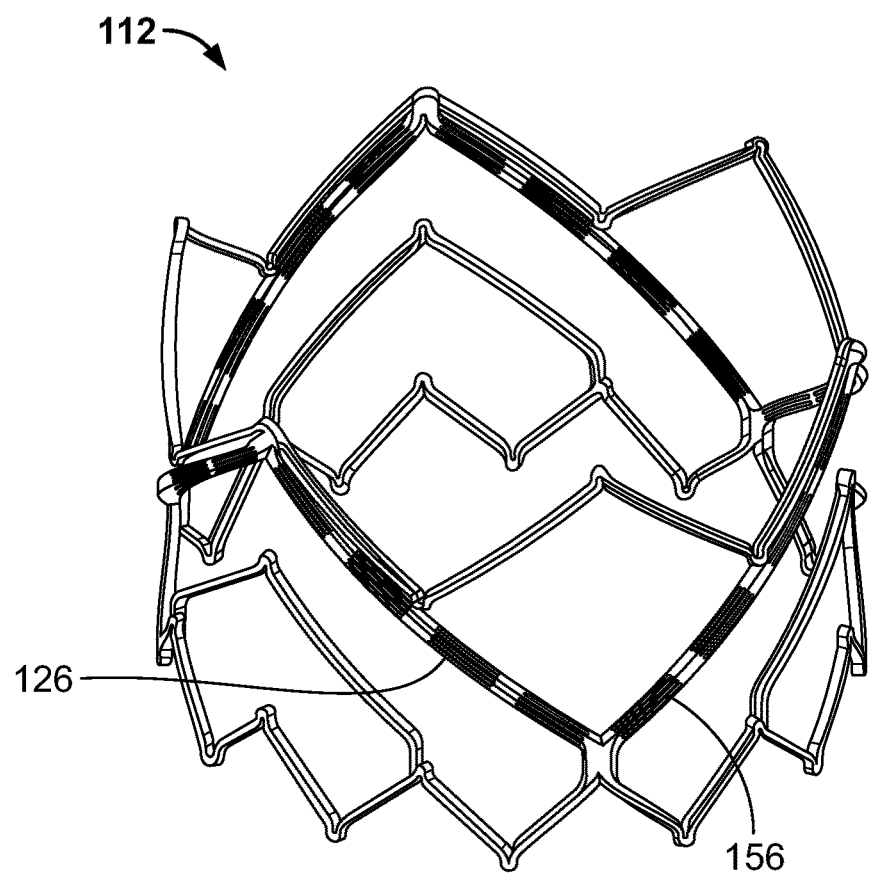

In one embodiment, the stent frame 112 shown in FIGS. 8, 9, and 10 may include specially formed slots to help securing the sheet of leaflet material to the stent frame 112. As shown in FIGS. 11 and 12, the stent frame 112 is similar to that shown in FIGS. 8 and 9, and includes slots 156 in the extended length wires 126.

Moreover, in the embodiment shown in FIGS. 11 and 12, when applied to the stent frame 112, the tube of leaflet material may be created using separate pieces of leaflet material that may be attached to each unit X of the stent frame 112 by inserting extensions from the material (not shown) into the specially formed slots 156 (shown in FIGS. 11 and 12) in the extended length wires 126.

Figure 13:
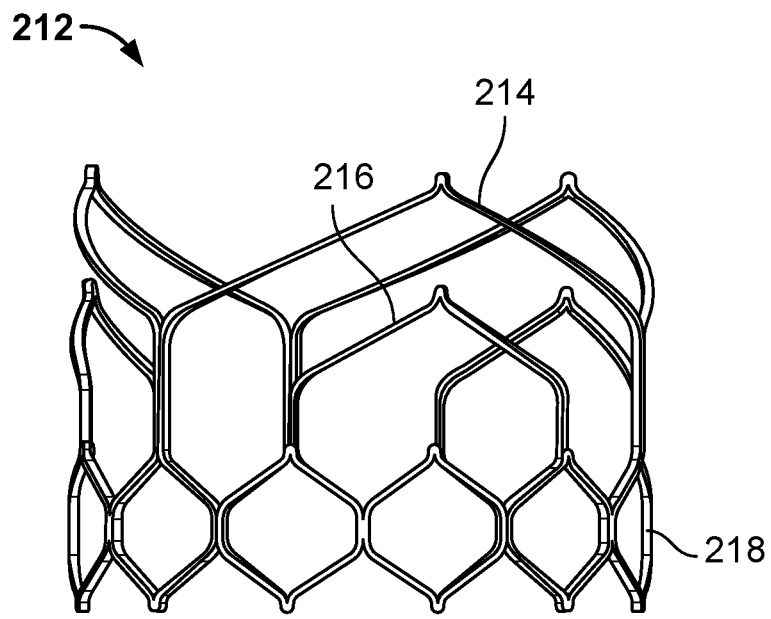
FIGS. 13, 14, 15 are respectively a front view, a perspective view, and a plan view of another embodiment of the stent frame, in accordance with an embodiment of the present disclosure.
Figure 14:
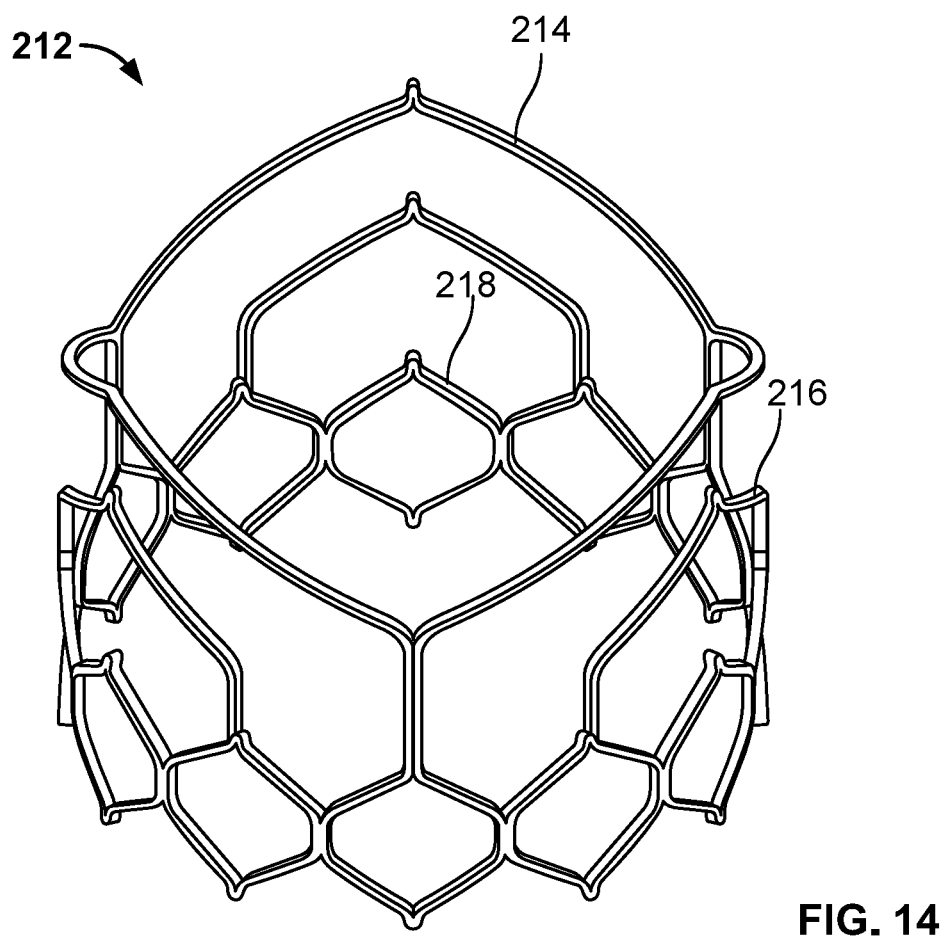
Figure 15:
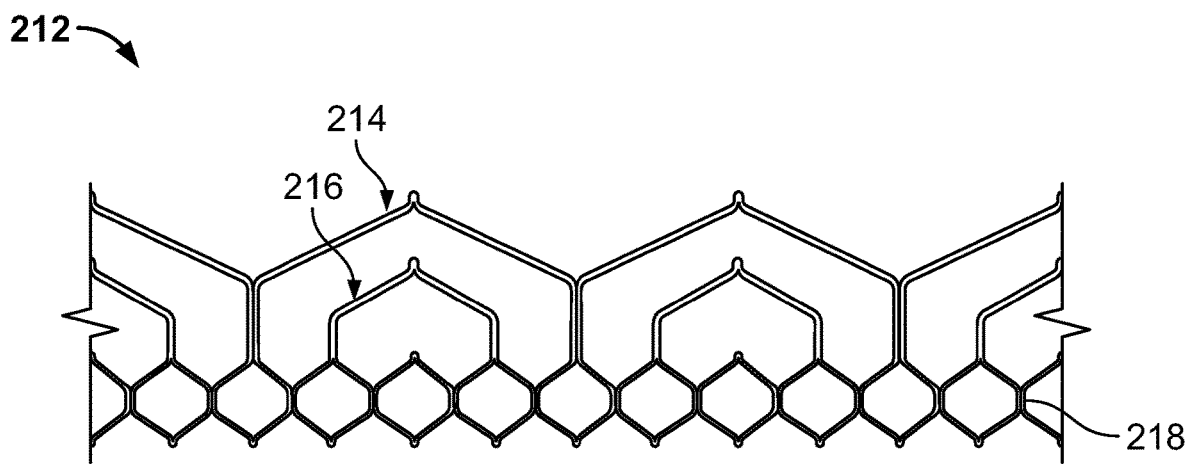

Referring now to FIGS. 13, 14, and 15, in this embodiment, the stent frame 212 includes three rows of connectors. Specifically referring to FIG. 15, the stent frame 212 may include a first set of three large roof-shaped upper connectors 214 (e.g., top row), a second set of three medium sized roof-shaped middle connectors 216 (e.g., middle row), a row of honey-comb shaped wires 88 forming the bottom of the stent frame 218 (e.g., bottom row). As an example, the stent frame 212 may have dimensions in millimeters (mm) as shown in FIG. 15 (e.g., each of the upper roof-shaped upper connectors 214 may be about 13.88 mm in length, each of the roof-shaped middle connectors 216 may be about 6.60 mm in length, etc.).

Figure 16:
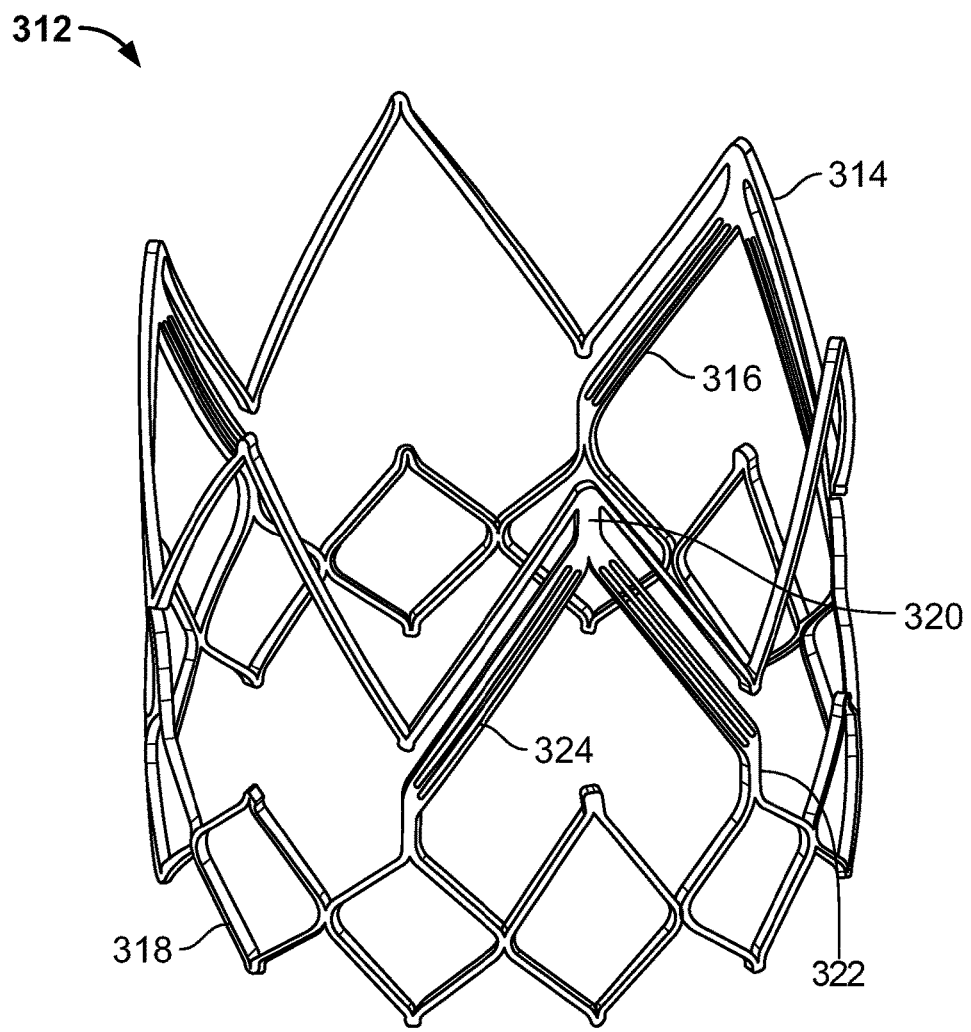
FIG. 16 is a perspective view of another embodiment of the stent frame, in accordance with an embodiment of the present disclosure.

In another embodiment, the frame may have another geometric design, illustrated as a stent frame 312 shown in FIG. 16. In this embodiment, the stent frame 312 may include a top row 314 of wires, a middle row 316, a bottom row 318 of wires, a first set of connectors 320 connecting the top row 314 of wires to the middle row 316 of wires, and a second set of connectors 322 connecting the middle row 316 of wires to the bottom row 318 of wires. The top row 314 of wires may include undulating plurality of similarly sized wires or struts. The middle row 316 of wires and the first set of connectors 320 may form a repeating roof-shaped design. The bottom row 318 of the wires may form a repeating diamond-shaped pattern or design. In certain embodiments, the stent frame 312 may include slots 324 in the middle row 316 of wires. The slots 324 may help securing the sheet of leaflet material to the stent frame 312 in a similar manner that the slots 156 help secure the sheet of leaflet material to the stent frame 212 as set forth above in FIGS. 11 and 12.

Figure 17:
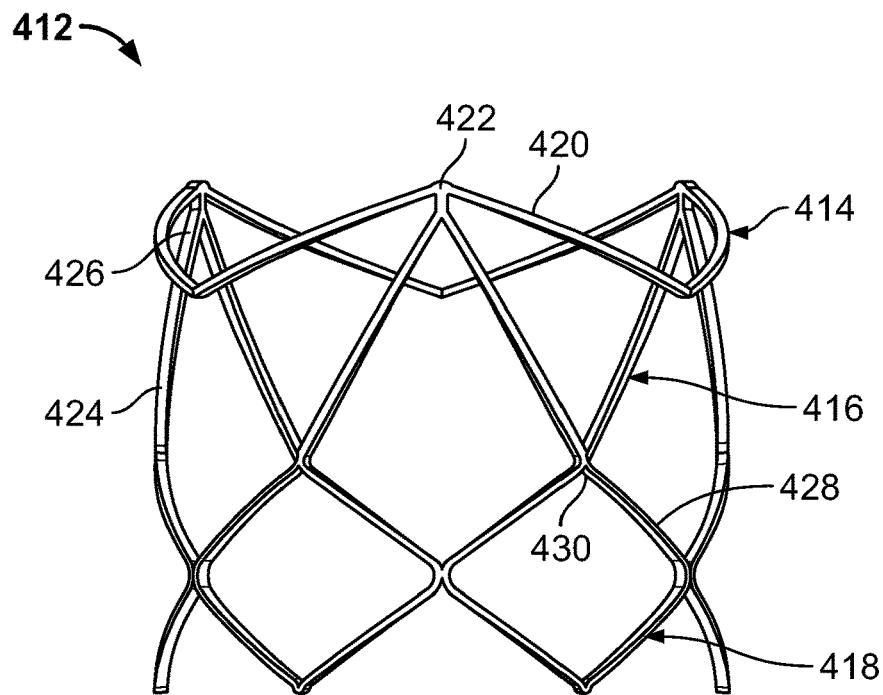
FIGS. 17, 18, and 19 are respectively a front view, a perspective view, and a plan view of another embodiment of the stent frame, in accordance with an embodiment of the present disclosure.
Figure 18:
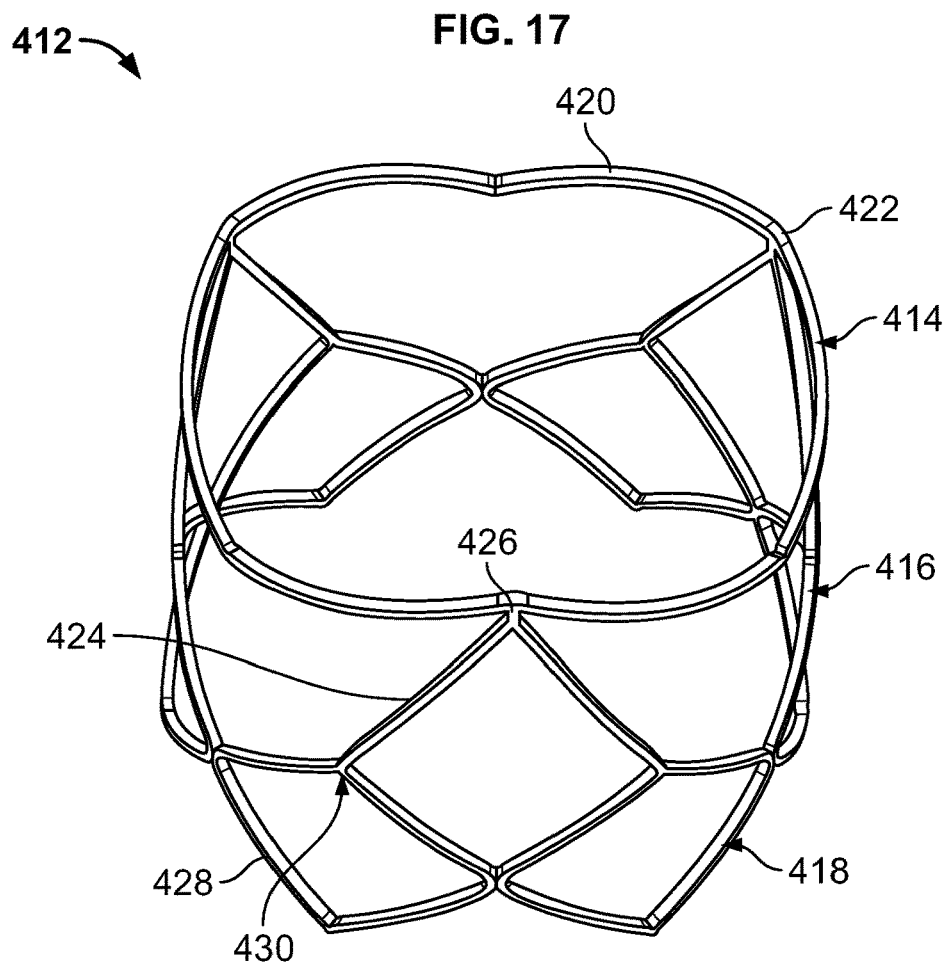
Figure 19:
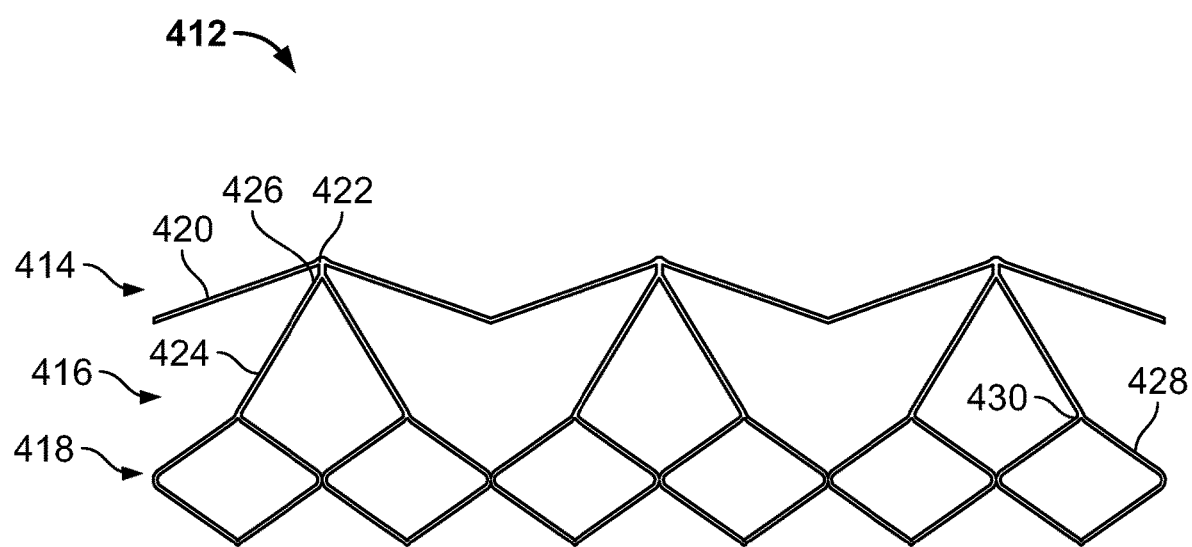

In yet another embodiment, the stent frame may have another geometric design, illustrated as a stent frame 412 shown in FIGS. 17, 18, and 19. In this embodiment, the stent frame 412 may include a top row of wires or struts 414, a middle row of wires or struts 416, and a bottom row of wires or struts 418. The top row of wires 414 includes an undulating plurality of similarly sized wires or struts 420, connected at the respective apexes 422. The middle row of wires 416 includes one or more pairs of upward-extending wires 424 connected at the respective apexes 426. The bottom row of wires 418 may form a repeating diamond shaped design with a plurality of diamonds 428 of a similar size.

Each of the one or more pairs of upward-extending wires 424 is connected to the top row of wires 414 at the respective apexes 422. For example, a short wire may connect the respective apex 422 of the top row of wires 414 to the respective apex 426 of the upward-extending wires 424. Each of the diamonds 428 in the bottom row 418 may be connected to the respective upward-extending wire 424 at the respective corner 430 of the diamond 428.

Figures 20, 21:
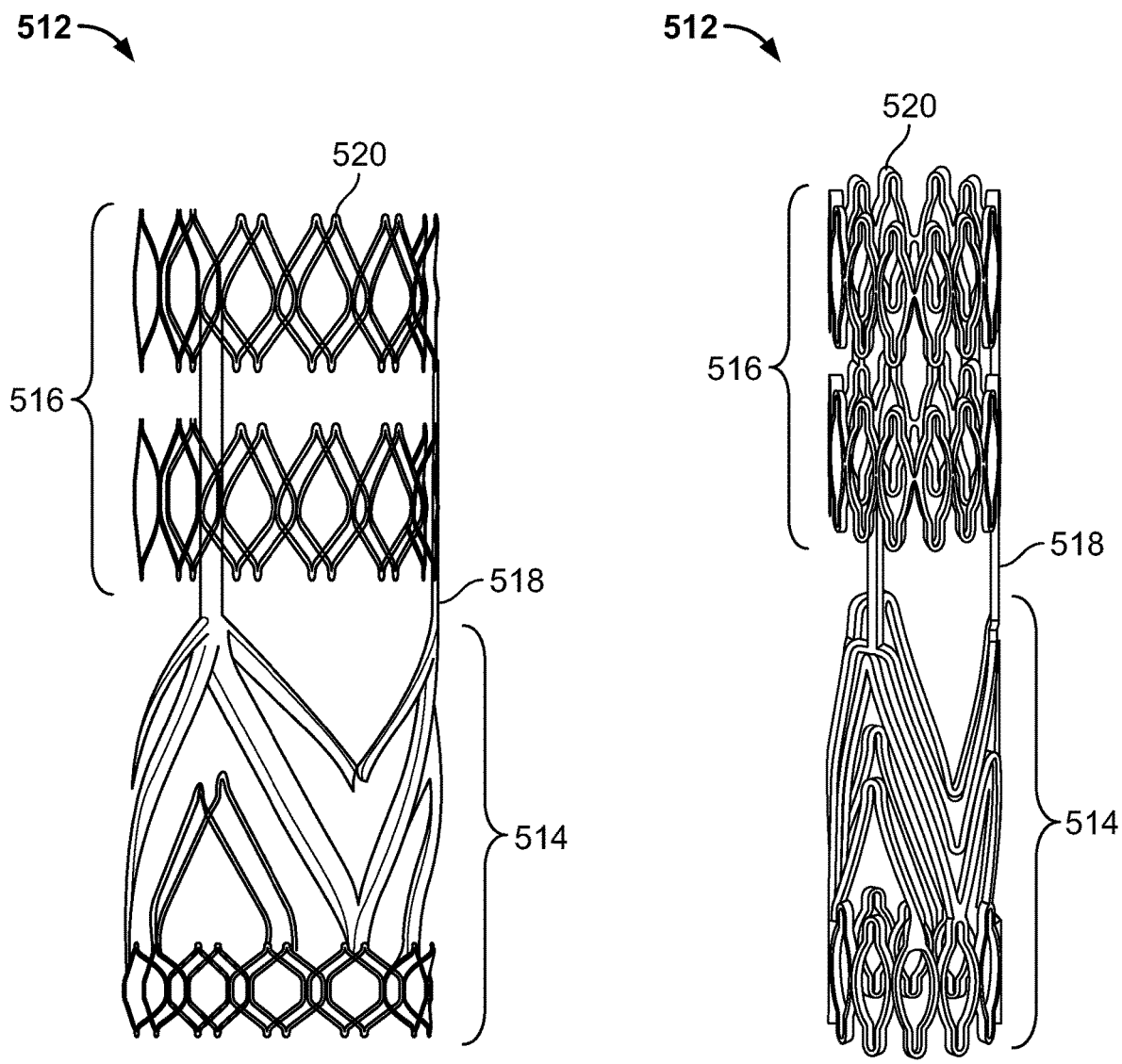
FIGS. 20 and 21 are respectively a front view and a perspective view of another embodiment of the stent frame, illustrating features configured to allow connecting the stent frame at a higher point in a patient's aorta, in accordance with an embodiment of the present disclosure.

In another embodiment, the stent frame may have another geometric design, illustrated as a stent frame 512 shown in FIGS. 20 and 21. In this embodiment, the stent frame 512 may include a lower portion 514 and an upper portion 516 for use for supra-annular deployment. Specifically, the lower portion 514 may be designed in any of the configurations disclosed herein with regard to stent frames 12, 112, 212, 312, and 412, and a combination thereof. In this embodiment, the lower portion 514 may be connected to the upper portion 516 by a plurality of vertical wire portions 518. The upper portion 516 may include one or more undulating wires 520 configured to allow connecting the stent frame 512 at a higher point in a patient's aorta, depending on the geometry of the patient's anatomy.

As shown in FIGS. 20 and 21, the stent frame 512 is configured with capability to expand and retract in the radial direction of the stent frame 512 as appropriate. As may be appreciated, any other designs of the stent frame disclosed herein (e.g., stent frames 12, 112, 212, 312, and 412) are also configured to expand and retract in the radial direction as appropriate. In practice, the TPHV 10 may be crimped onto a balloon catheter or any other suitable delivery device by any suitable method known in the art. The TPHV 10 may also be deployed as a self-expandable stent with a suitable delivery device. It should be appreciated that due to the unique geometry of the stent frame (e.g., the stent frames 12, 112, 212, 312, and 412), there is less chance for the sheet of leaflet material (the leaflet material 58) to be ripped or stretched when crimped on to the delivery device. In addition, the geometries of the stent frame (e.g., the stent frames 12, 112, 212, 312, and 412) allow the TPHVs 10 to be crimped in to a smaller diameter than other commercially available devices. In some embodiments, the TPHVs 10 disclosed herein may have an inner diameter and a height (e.g., along the axial direction), and the ration of the height to the inner diameter is in a range between about 0.5 and about 0.9, when the TPHVs 10 are substantially fully expanded.

It should also be appreciated that the tube of leaflet material (the leaflet material) may be disposed on the stent frames (e.g., the stent frames 112, 212, 312, 412, and 512) disclosed herein in a similar manner as set forth above in FIGS. 1, 2, 3 and 4. In particular, the tube of leaflet material (the leaflet material) may be woven through the stent frame disclosed herein (e.g., the stent frames 112, 212, 312, 412, and 512) as appropriate. For example, at least a portion of the sheet of leaflet material may be tucked in under the top row of wires as the sheet of leaflet material is woven through the stent frame. At least a portion of the sheet of leaflet material (the leaflet material) may be tucked in under the top row of wires between the first set of connectors.

In some embodiments, the sheet of leaflet material (the leaflet material) may be disposed on the exterior of the stent frame and generally wrap around the top edge portion and bend or fold towards the interior of the stent frame (e.g., without woven through the stent frame). In some embodiments, the sheet of leaflet material (the leaflet material) may be disposed on the interior of the stent frame and at the proximity of the top edge portion, folds or bends towards the interior (e.g., with or without woven through the stent frame). In some embodiments, the stent frames disclosed herein (e.g., the stent frames 12, 112, 212, 312, 412, and 512) may be used in combination with an outer skirt to prevent leaking.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available or prudent in manufacturing. To the extent that the term "operably connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. A transcatheter prosthetic heart valve, comprising:
a stent frame comprising a top portion and a bottom portion; and
a tube of leaflet material configured to encircle the stent frame; wherein the tube of leaflet material comprises:
a lower portion disposed about an exterior surface of the stent frame; and
an upper portion that is at least partially disposed within an interior surface of the stent frame; and
wherein the upper portion disposed within the stent frame forms at least one leaflet capable of moving from a first position to a second position within the stent frame,
wherein at least a portion of the upper portion of the tube of leaflet material wraps around a connection point of the top portion and folds towards the interior surface of the stent frame; and
at least a second portion of the tube of leaflet material weaves under an upper edge of the top portion of the stent frame and folds towards the interior surface of the stent frame.

2. The transcatheter prosthetic heart valve of claim 1, wherein the tube of leaflet material is formed from a continuous sheet of leaflet material, and an upper edge of the continuous sheet of leaflet material comprises at least three arches extending upwardly therefrom.

3. The transcatheter prosthetic heart valve of claim 2, wherein the upper edge of the continuous sheet of leaflet material comprises a space between each of the at least three arches.

4. The transcatheter prosthetic heart valve of claim 1, wherein the tube of leaflet material is formed from two or more pieces of leaflet material.

5. The transcatheter prosthetic heart valve of claim 1, wherein the tube of leaflet material is extruded.

6. The transcatheter prosthetic heart valve of claim 1, wherein the tube of leaflet material comprises a polymer material.

7. The transcatheter prosthetic heart valve of claim 6, wherein polymer material comprises linear low density polyethylene, polytetrafluoroethylene, low-density polyethylene, polyethylene terephthalate, polypropylene, polyurethane, polycaprolactone, polydimethylsiloxane, polymethylmethacrylate, polyoxymethylene, thermoplastic polyurethane, and combinations thereof.

8. The transcatheter prosthetic heart valve of claim 7, wherein the polymer material is linear low density polyethylene.

9. The transcatheter prosthetic heart valve of claim 8, wherein the tube of leaflet material comprises a polymer material and hyaluronic acid.

10. The transcatheter prosthetic heart valve of claim 1, wherein the tube of leaflet material comprises a bioprosthetic material.

11. The transcatheter prosthetic heart valve of claim 1, wherein the leaflet has a three dimensional curvature.

12. The transcatheter prosthetic heart valve of claim 11, wherein the leaflet has a two dimensional surface.

13. The transcatheter prosthetic heart valve of claim 1, wherein the stent frame is expandable.

14. The transcatheter prosthetic heart valve of claim 13, wherein the stent frame is self-expandable.

15. The transcatheter prosthetic heart valve of claim 13, wherein the stent frame is balloon expandable.

16. The transcatheter prosthetic heart valve of claim 1, wherein the stent frame has a height and an inner diameter, and wherein a ratio of the height to the inner diameter is in a range between about 0.5 and about 0.9.

* * * * *